United States Patent [19]

Armstrong

[11] Patent Number: 5,312,900
[45] Date of Patent: May 17, 1994

[54] 23K PROTEIN WITH BINDING SPECIFICITY FOR QUEUINE

[75] Inventor: R. Douglas Armstrong, Encinitas, Calif.

[73] Assignee: La Jolla Cancer Research Foundation, La Jolla, Calif.

[21] Appl. No.: 681,889

[22] Filed: Apr. 8, 1991

[51] Int. Cl.$^5$ .......................... C07K 15/00; C07K 3/18
[52] U.S. Cl. .................................. 530/350; 530/412; 530/413; 530/851
[58] Field of Search ................. 530/350, 412, 413, 851

[56] References Cited

U.S. PATENT DOCUMENTS 4,571,423  2/1986  Nomura et al. ...................... 544/280
4,595,530  6/1986  Nishimura et al. .................. 544/280

OTHER PUBLICATIONS

Kuchino et al "Preparation and Characterization of Monoclonal Antibodies for the Modified Base Queine" Proc. Jnp. Acad. 63 1987, pp. 393–396.

Kuchino et al "Monoclonal Antibodies to Queine" Nuc Acid Res 16 1985 221–223.

Harlow et al "Antibodies A Laboratory Manual" Cold Spring Harbor Lab, 1988, p. 313.

Kasai et al., Distribution of the modified nucleoside Q and its derivatives in animal and plant transfer RNA's. Nucl. Acids Res. 2:1931–1939 (1975).

Katze et al., Queuine, a modified base incorporated posttranscriptionally into eukaryotic transfer RNA: wide distribution in nature. Science 216:55–56 (1982).

Okada et al., Novel mechanism of post-transcriptional modification of tRNA. J. Biol. Chem. 254:3067–3073 (1978).

Okada and Nishimura, Isolation and characterization of a guanine insertion enzyme, a specified tRNA transglycosylase, from *Escherichia coli.* J. Biol. Chem. 254:3061–3066 (1978).

French et al., Queuine, a tRNA anticodon wobble base, maintains the proliferative and pluripotent potential of HL-60 cells in the presence of the differentiating agent 6-thioguanine. Proc. Natl. Acad. Sci. USA 38:370–374 (1991).

Langgut and Kersten, The deazaguanine-derivative, queuine, affects cell proliferation, protein phosphorylation and the expression of the proto oncogenes c-fos and c-myc in Hela cells. FEBS 265:33–36 (1990).

Randerath et al., Speicific lack of the hypermodified nucleoside, queuosine, in hepatoma mitochondrial aspartate transfer RNA and its possible biological significance. Cancer Res. 44:1167–1171 (1984).

Bienz et al., Wild-type tRNA$^{Tyr}$ reads the TMV RNA stop codon, but Q base–modified tRNA$^{Tyr}$ does not. Nature 294:188–190 (1981).

Emmerich et al., Relationship of queuine-lacking transfer RNAs to the grade of malignancy in human leukemias and lymphomas. Cancer Res. 43:4308–4314 (1985).

Katz and Farkas, A factor in serum and amniotic fluid is a substrate for the tRNA-modifying enzyme tRNA-guanine transferase. Proc. Natl. Acad. Sci. USA 76:3271–3275 (1979).

Singhal, Queuine: an addendum. Progress in Nucleic Acids Research and Molecular Biology 28:75–80.

Nishimura et al., Characterization and analysis of oncofetal tRNA and its possible application for cancer diagnosis and therapy. Recent Results in Cancer Research. 84:401–412 (1983).

Akimoto et al., Queuine analogues: their synthesis and inhibition of growth of mouse L5178Y cells in vitro. J. Med. Chem. 29:1749–1753 (1986).

*Primary Examiner*—Christine M. Nucker
*Assistant Examiner*—Chris Dubrule
*Attorney, Agent, or Firm*—Campbell and Flores

[57] ABSTRACT

The invention generally relates to the discovery of a 23 kD protein, designated herein as Queb, that has specific binding affinity for the purine base Queuine. The invention particularly relates to polypeptides having specific binding reactivity with Queuine and methods of using such polypeptides to purify Queuine and Queuine-containing substances. The invention also relates to antibodies having specific reactivity with Queuine or Queb. Methods for determining the presence and concentration of Queuine and Queb are also provided as well as methods for the diagnosis of a pathological disease or prognosis of a patient having a disease associated with Queuine, Queuine-containing substances such as Queuine-tRNA, or Queb. Kits useful for performing the methods of the present invention are also provided.

5 Claims, 3 Drawing Sheets

23K PROTEIN WITH BINDING SPECIFICITY FOR QUEUINE

This invention was made with United States government support under Grant No. CA-46550 awarded by the National Institute of Health. The United States government has certain rights in this invention.

BACKGROUND OF THE INVENTION

One of the more unique purines occurring in nature is the base known as Queuine, which is a 7-deaza mammalian cells, Queuine cannot be synthesized by such cells. Instead, Queuine is believed to be obtained from the diet or gastrointestinal microflora as discussed in Nishimura, *Proc. Nucleic Acid Res.* 28:49-80 (1983). In addition to mammalian systems, Queuine is found widely distributed in nature, including plants, bacteria and other eukaryotic cells such as Tetrahymena and *Dictyosterium discoideum* as reported in Kasai et al., *Nucleic Acids Res.* 2:1931-1939 (1975); Farkas, *Nucleosides & Nucleotides* 2:1-20 (1983); and Katze et al., *Science* 216:55-56 (1982).

The primary biochemical role of Queuine is reported to be its presence in the wobble position of tRNA that have isoacceptors for tyrosine, histidine, asparagine and aspartic acid. The mechanism for insertion of Queuine at these sites has been well characterized and has been found to occur through the post-transcriptional action of a transglycosylase reaction as described in Okada et al., *The Journal of Biological Chemistry* 254:3067-3073 (1978); Okada and Nishimura, *The Journal of Biological Chemistry* 254:3061-3066 (1978).

The role of Queuine in the wobble position of tRNA has not yet been elucidated. However, there is speculation that Queuine may have a role in cell development or as a putative growth factor as discussed in Nishimura, supra: French et al., *Proc. Nat'l Acad. Sci U.S.A.* 38:370-374 (1991); and Langgut & Kersten, *FEBS* 265: 33-36 (1990). The role of Queuine may be related to Queuine itself, to its tRNA incorporation or to other Queuine-containing substances. A structural relationship has been suggested with active phorbol ester tumor promoters such as TPA, teleocidin A and phorbol 12,13-didecanoate (PDD). In addition, Queuine has been shown to affect phorbol ester pharmacology. Queuine can also inhibit the activity of 6-thioguanine in repressing cell growth as recently reported in French et al., *Proc. Nat'l Acad. Sci. U.S.A.* 38:370-374 (1991). Queuine has further been reported to inhibit the differentiation of HL-60 cells by inhibiting the insertion of 6-thioguanine into the wobble position.

Of interest has been the observation that in all animal neoplastic cells examined thus far, including cells transformed in vitro, the tRNAasp, asg, hist, tyr are deficient, or hypomodified, in Queuine. This observation was nicely demonstrated by Randerath et al., *Cancer Res.* 44: 1167-1171, 1984, who isolated tRNA from normal and from malignant rat liver cells. They completed a full sequence analysis of the tRNAasp and observed that the tRNA from the normal cells had a Queuine molecule in the wobble position, but the wobble position of the tRNA from the malignant cells contained only guanine. These results suggest that Queuine-tRNA (Q-tRNA) deficiency may be tumor specific for a particular tissue. Speculation about the role that Queuine-deficiency might have in mediating the neoplastic state has been made, although a precise function of Q-tRNA has not been identified, and Queuine deficient cells appear to grow normally as reported, for example, in Bienz et al., *Nature* 294:188-190, 1981).

Although several studies have demonstrated Q-tRNA deficiency in rodent cancers, confirmation that this may occur in undeveloped human tissues has only been suggested in a study by Emmerich et al., *Cancer Res.* 45:4308-4314, 1985. This study, completed with human lymphomas and chronic stage leukemias, concluded that "decreased Queuine content of tRNA may not be a general feature of neoplasms, but it may be important for disease activity and perhaps also for the state of maturation in human lymphomas and leukemias". The characterization of which types or stages of human cancers are Queuine deficient is of importance and potential therapeutic value.

Another aspect of Queuine biology that has not been characterized is its biodistribution. Mammalian physiological concentrations of Queuine are generally low ranging from 1 to 10 nM with the exception of third trimester bovine amniotic fluid as reported in Katze et al., Supra: Emmerich et al., *Cancer Res.* 45:4308-4314 (1985). The concentration of Queuine in such late stage bovine amniotic fluid (BAF) is over 100-fold relative to its concentration in fetal bovine serum (FBS) or other body fluids. The high concentration of Queuine in the later stages of BAF additionally suggests that Queuine has a role in embryonal or cell development. However, the mechanism by which the concentration phenomenon is achieved has not been identified.

Studies evaluating the biochemistry of Queuine and Q-tRNA have been limited by the absence of reagents. More particularly, such limitations are related to the relative unavailability of Queuine and the lack of a simple and sensitive detection system for Queuine and Q-tRNA. Queuine must generally be isolated from natural sources that contain low concentrations of Queuine. In addition, the quantitative analysis of Queuine and Q-tRNA has been dependent upon a complicated bioassay described in Katze and Farkas, *Proc. Natl. Acad. Sci. USA* 76:3271-3275 (1979). Both procedures are limited, difficult and time-consuming. These limitations adversely affect the ability to produce sufficient quantities of Queuine for various purposes and severely limit the scientific evaluation of Queuine and its biological activity.

The availability of a Queuine-specific antibody or binding protein would be of tremendous help in this regard. However, prior to the present invention, antibodies or binding proteins effective for analysis of Queuine have not been produced. As a naturally occurring compound, Queuine does not serve as an effective antigen.

Thus, a need exists for methods of detecting and analyzing Queuine, Queuine-tRNA and other Queuine-containing substances with simple and sensitive assay systems. In addition, methods of obtaining large quantities of Queuine are also needed. The present invention satisfies these needs and provides related advantages as well.

SUMMARY OF THE INVENTION

The present invention is directed to a novel polypeptide having specific binding reactivity with Queuine such that it can bind to Queuine alone or to Queuine-containing substances. The polypeptide can be a substantially pure form of a naturally-occurring protein, designated herein as Queb, having a molecular weight of about 23 kilodaltons (kD) as determined by SDS- PAGE. Antibodies having specific reactivity with Queuine and the novel Queuine-specific polypeptides of the present invention are also provided.

Methods for purifying the polypeptide of the present invention are also provided in which Queuine, a Queuine-containing substance or an antibody is used to isolate the polypeptide from other components. Conversely, the present invention is also directed to methods for purifying Queuine and Queuine-containing substances in which the novel polypeptide or an antibody having specific reactivity with Queuine is used to isolate Queuine and Queuine-containing substances.

The present invention further relates to methods for determining the presence or concentration of Queuine or Queuine-containing substances in biological systems such as animals, including humans, and plants. Such methods include the in vitro detection of Queuine or Queuine-containing substances in fluids, tissues and cells, including normal and malignant cells. The methods also include the in vivo imaging of Queuine, Queuine-containing substances or Queb in a patient. Because of its specificity for Queuine, which has been associated with embryonic development, Queb can be used as an embryonic marker.

The methods of the present invention can also be used for the diagnosis of a disorder or prognosis of a patient having or suspected of having a disease or disorder associated with abnormal levels of Queuine or Q-tRNA deficiency in which the amount of Queuine or a Queuine-containing substance, such as Queuine-tRNA, detected is correlated with the diagnosis of a disorder or prognosis of the patient.

In a further aspect of the present invention, Queb can be used as the diagnostic or prognostic indicator in which the amount of Queb in a patient having or suspected of having a disorder associated with abnormal levels of Queb is correlated with the diagnosis of a disorder or the prognosis of the patient.

The present invention further relates to methods of regulating cell development and differentiation by regulating the activity of Queuine, Queuine-containing substances or Queb. Relatedly, the adverse effects of a toxic Queuine-containing substance can be inhibited by administering Queb as an antidote. Methods for reducing the binding affinity of Queuine to Queb are also provided.

Finally, kits containing Queuine, Queuine-containing substances, or the novel polypeptides useful in the methods of the present invention are also provided. The kits can additionally contain ancillary reagents necessary to accomplish the present methods.

DETAILED DESCRIPTION OF THE INVENTION

The present invention generally relates to an unexpected discovery of a protein designated herein as "Queb," having specificity and binding affinity for Queuine. The protein was initially isolated by affinity chromatography from third trimester bovine amniotic fluid (BAF).

Figure 1:
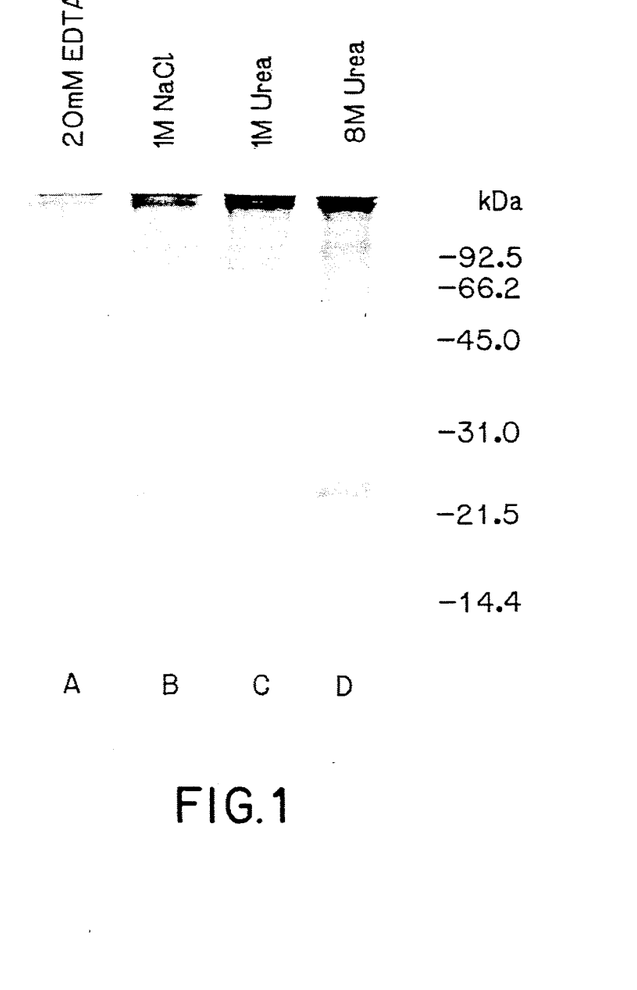
FIG. 1 shows the electrophoretic analysis of BAF proteins bound to Queuine-sepharose. The proteins derived from bovine amniotic fluid (BAF) and eluted from Queuine-sepharose was analyzed with 15% SDS-PAGE. The gel was stained with Coomassie blue and photographed. The elution conditions included: (A) 20 mM EDTA; (B) 1 mM NaCl; (C) 1M urea; and (D) 8M urea.

The well known CNBr-coupling procedure was used to couple Queuine to sepharose. This procedure allowed the cyclopentenediol portion of the Queuine molecule to be free as has been reported to occur when Queuine is incorporated into tRNA. Thus, the Queuine sepharose compound mimics Q-tRNA and other Queuine-containing substances. In addition, the coupling procedure utilizes the 2-amino group of the purine ring, which is common to both Queuine and the structurally related purine, guanosine. As shown in FIG. 1, Queb remained bound to Queuine-sepharose under weak eluting conditions of 20 mM EDTA, 1 M NaCl and 1 M urea and eluted only under stringent elution conditions of 8 M urea. The elution profile suggests that Queb's binding affinity for Queuine and Queuine-containing substances is high.

Queb has an approximate molecular weight in the range of 22 to 25 kD, and more particularly about 23 kD. The approximate molecular weight of Queb was determined from a 15% SDS-PAGE analysis of the protein isolated from third trimester BAF, the results of which are shown in FIG. 1. Using standard amino acid sequence analysis, Queb was determined to have the following internal amino acid sequence: EGSDNQPNGXTNPN (SEQ ID No. 1). Based on its apparent molecular weight and amino acid content, Queb appears to be a previously uncharacterized protein.

The specificity of Queb binding for Queuine was tested by substituting guanosine for Queuine. Again, the same CNBr-coupling procedure was used to derivatize the 2-amino group of the purine ring. Queb did not bind to guanosine-sepharose in contrast to its high binding affinity for Queuine-sepharose. These results suggest that Queb has selectivity for binding to Queuine compared with structurally similar purines such as guanosine.

In addition, these results indicate that Queb is not the well-characterized mammalian enzyme, tRNA-guanine transglycosylase (EC 2.4.2.29). This enzyme serves to irreversibly insert Queuine into the wobble position of certain tRNA. The transglycosylase has also been shown to readily accept other purines as substrates. Such substrates can strongly compete with Queuine for insertion into tRNA. As indicated above, Queb has been shown to be highly specific for Queuine and therefore does not appear to be related to the transglycosylases since neither its size or ligand affinity appear to be related to that demonstrated for the transglycosylase as reported in Singhal, *Progress in Nucleic Acids Research and Molecular Biology*, 28:75-80 (1983).

Thus, one aspect of the present invention relates to substantially pure polypeptides having specificity and binding affinity for Queuine. The polypeptides of the present invention have specific binding affinity for Queuine alone or for Queuine-containing substances. Such Queuine-containing substances can include, for example, RNA, proteins, peptides, polymers, such as sepharose, drugs, toxins, inorganic substances and the like in which Queuine is incorporated into the substance or complexed or conjugated with the substance.

These novel polypeptides, also referred to herein as "Queuine-specific polypeptides," include a substantially pure form of Queb or a fragment thereof and other polypeptides substantially having the specificity and binding affinity of Queb. As used herein, "substantially pure" means polypeptides that are essentially free of other biochemical substances with which it is normally associated in nature or essentially free of reagents used or arising from the preparation of such polypeptides. Such substantially pure polypeptides can be purified from a native source, synthesized or produced biologically or recombinantly by means known to those skilled in the art.

For example, a desired polypeptide can be obtained or prepared by any biological means known to those skilled in the art including, without limitation, active proteolysis of the naturally-occurring Queb protein with chemical reagents or enzymes known in the art. Alternatively, the synthetic formation of a polypeptide involves the chemical synthesis of any desired chain of amino acids and can also be accomplished by any method known in the art. Production of polypeptides by recombinant methods can also be accomplished by any methods known in the art.

The Queuine-specific polypeptides of the present invention can have the internal amino acid sequence: EGSDNQPNGXTNPN (SEQ ID No. 1). Queuine-specific polypeptides having substantially this internal sequence or other internal sequences are also with the scope of the present invention. "Substantially the amino acid sequence" includes the above sequence or other sequences having additions, deletions or substitutions that do not substantially reduce the specificity or binding affinity of the polypeptides relative to the native protein, Queb.

The present invention further relates to methods of purifying and isolating Queuine-specific polypeptides to produce substantially pure polypeptides. The methods of the present invention can use the principles of affinity chromatography, which include the steps of (a) contacting a sample containing the polypeptide to be purified with insoluble Queuine or antibody having specific reactivity with the polypeptide; (b) separating bound polypeptide from unbound components of the sample; (c) detaching bound polypeptide from the insoluble Queuine or antibody; and (d) collecting purified polypeptide. These methods can be used for purifying naturally occurring Queb or other Queuine-specific polypeptides of the present invention. The sample can be obtained or derived from BAF, particularly third trimester BAF.

In one embodiment of the purification methods, Queuine is coupled to sepharose by a CNBr-coupling procedure known in the art. Queuine can also be insolubilized by attachment to a solid substrate, such as beads, microparticles, plates, tubes and membranes, for example, by means known in the art. The sample can be contacted with the insoluble Queuine by mixing the sample with the insoluble Queuine or by pouring the sample over a column containing the insoluble Queuine. The bound polypeptide can be detached from the insoluble Queuine by any method known in the art including, for example, eluting with a strong eluent such as 8 M urea or guanidine-HCl, for example. Alternatively, a phorbol ester tumor promoter can be used to lower the binding affinity of Queuine and a Queuine-specific polypeptide such that a milder eluent can be used.

Queuine or a Queuine-containing substance can likewise be purified according to the above methods of the present invention, which include the steps of:

(a) contacting a sample containing Queuine or the Queuine-containing substance to an insolubilized polypeptide having specific binding reactivity with Queuine but substantially non-cross reactive with non-Queuine moieties;

(b) separating bound Queuine or the Queuine-containing substance from unbound components of the sample;

(c) detaching bound Queuine or the Queuine-containing substance from said insolubilized polypeptide; and (d) collecting purified Queuine or the Queuine-containing substance.

The sample can similarly be obtained or derived from sources containing Queuine such as, for example, third trimester BAF. Other known sources of Queuine are identified in Katze et al., *Science* 216:55–56 (1982).

The insolubilized polypeptide of these methods can be naturally occurring Queb, any Queuine-specific polypeptide of the present invention or antibodies having specific reactivity with Queuine. Such insolubilized polypeptides are substantially non-cross reactive with non-Queuine moieties. The term "substantially non-cross reactive with non-Queuine moieties" means insolubilized polypeptides are reactive only with Queuine or the Queuine-containing substances of the present invention and are not cross-reactive with other substances to a degree that would substantially affect the isolation of Queuine or Queuine-containing substances from other components in the sample.

In one embodiment, purified Queb can be insolubilized by CNBr-coupling to sepharose or by attachment to various solid substrates, such as those previously identified, according to methods known in the art.

Queuine and Queuine-containing substances substantially purified by the methods of the present invention can be used for a variety of purposes. For example, substantially purified Queuine can be used as a vitamin or a food supplement. Although a component of normal animal cells, Queuine must be obtained from external sources as previously noted. Purified Queuine can also be used for potential therapeutic applications as a cell growth regulatory agent and for continued scientific investigation into the functional activity of Queuine and Q-tRNA as well as investigating the activities of Queb. Prior to the present invention, scientific evaluations were hindered by the lack of adequate amounts of purified Queuine.

Purified Queuine-specific polypeptides, including Queb, can additionally be used as immunogens to produce antibodies that would be useful for the diagnosis, prognosis and therapy of a subject having or suspected of having a disorder associated with Queuine, Q-tRNA or Queb.

Antibodies having specificity and binding affinity for Queuine or Queuine-specific polypeptides can be obtained by techniques well known in the art. Such antibodies can be polyclonal or monoclonal. Particularly useful antibodies have specificity for Queuine, Queb or a Queb-Queuine complex. Anti-Queb antibodies can have specificity for the Queuine binding site of Queb and are thus idiotype antibodies of Queuine. Such idiotype antibodies can be used as immunogens to stimulate anti-Queuine antibody production. Other anti-Queb antibodies can have specificity for Queb at a non-Queuine binding site. These latter anti-Queb antibodies can be particularly useful in detecting Queb-Queuine complexes as well as free Queb.

Polyclonal antibodies can be produced, for example, by methods described in Ghose et al., *Methods in Enzymology*, 93:326-327 (1983), which is incorporated herein by reference. For example, purified Queuine or Queb can be used as the immunogen to stimulate the production of polyclonal antibodies in the antisera of animals such as rabbits, goats, sheep, rodents and the like.

Monoclonal antibodies can be produced by the general method described in Milstein & Kohler, *Nature* 256:495-97 (1975) or as modified in Gerhard, *Monoclonal Antibodies* 370-71 (Plenum Press, 1980), which are incorporated herein by reference. Briefly, the methods for producing such monoclonal antibodies include:

(a) immunizing a host capable of producing antibodies with substantially purified Queuine-specific polypeptide;

(b) fusing spleen cells of the immunized host with suitable myeloma cells to produce a mixture of hybridoma cells;

(c) culturing the hybridoma cells in a suitable media selective for hybridoma cells;

(d) selecting and cloning the hybridoma cells expressing monoclonal antibodies having specific reactivity for the Queuine-specific polypeptide; and (e) harvesting the monoclonal antibody thus produced.

Other methods of producing antibodies known in the art can also be used. Such methods include, for example, those described in the Huse et al., *Science* 246:1275-1281 (1989), incorporated herein by reference.

The present invention further relates to methods of detecting Queuine or Queuine-containing substances, such as Queuine-tRNA, in a sample, which includes the steps of (a) contacting a sample with a detectable substance having specific binding affinity for Queuine; and (b) detecting the binding of the polypeptide to the sample, wherein polypeptide binding indicates the presence of Queuine or Queuine-containing substance in the sample. The detectable polypeptide can be a binding protein, such as Queb, a Queuine-specific polypeptide of the present invention or an antibody. The methods can also be used to quantify the concentration of Queuine in a sample by further detecting the amount of polypeptide bound to the sample and relating the amount of binding to the concentration of Queuine in the sample. Alternatively, these methods can be used to detect and quantify Queb or other Queuine-specific polypeptides by using detectable Queuine, a Queuine-containing substance or anti-Queb antibodies. In a further aspect, the method can be used to detect Queuine-Queb complexes by using antibodies specific for such complexes.

As used herein, a "sample" can be obtained from various animal sources such as amniotic fluid, serum, plasma, whole blood, urine, ascites cells, cell extracts, tissue specimens and from plants such as plant fluids, cells and extracts. A "sample" also includes any prepared liquid to be analyzed for the presence or concentration of Queuine, Queuine-containing substances, Queb or other Queuine-specific polypeptides for use as controls, calibers and other various purposes for which a Queuine-containing solution is desired. A sample can also be tested for Queuine contamination.

Assays useful in the methods of the present invention for detecting or quantifying Queuine, queuine-containing substances, Queb or Queuine-specific polypeptides can be any assay known to those skilled in the art that is based on a ligand-receptor type of interaction. For example, various precipitation assays known in the art can be used. In addition, assays comparable to conventional immunoassays can be used such as the well known enzyme linked immunosorbent assays, radioassays, agglutination assays as described in U.S. Pat. No. 4,486,540, and sandwich assays as described, for example in U.S. Patent No. 4,376,110.

Conventional histological staining techniques can also be used for detecting Queuine, Queuine-containing substances, Queb or other Queuine-specific polypeptides in tissue samples. For example, a tissue specimen can be fixed in formalin, B-5 or other standard histological preservatives, dehydrated and embedded in paraffin according to standard procedures. Sections can then be cut from the paraffin and mounted on glass slides. Queuine, Queuine-containing substances or Queb can then be detected and localized by exposure to labeled polypeptides. Alternatively, frozen sections can be used to carry out the histological evaluation of tissue specimens and cells.

The antibodies and other polypeptides of the present invention can be made detectable by any of the methods known in the art, including the use of labels. Such labels include, for example, radioisotopes, enzymes, fluorogens, chromogens and chemiluminescent labels. For radioassays, suitable labels include tritium, carbon 14, phosphorous 32, iodine 125 or 131, yttrium-90, technetium-99 or sulfur 35. Examples of various suitable radioactive labels are described in U.S. Pat. No. 4,062,733, incorporated herein by reference.

Examples of various enzymatic labels include alkaline phosphatase, horseradish peroxidase, luciferase, beta-galactosidase, glucose oxidase, lysozyme, malate dehydrogenase and the like. Suitable substrates for the enzymatic systems depend on the enzyme used and can be determined by those skilled in the art. Examples of such substrates include, for example, simple chromogens and fluorogens such as para-nitrophenyl phosphate, beta-D-glucose, homovanillic acid, o-dianisidine, bromocresol purple, 4-methyl-umbelliferone and indoxyl phosphate.

Chromogen labels are compounds that absorb light in the visible ultraviolet wavelengths. Such compounds are usually dyes. Fluorogenic compounds emit light in the ultraviolet or visible wavelength subsequent to irradiation by light or other energy source. A representative listing of suitable fluorogens are described in U.S. Pat. No. 4,366,241 and U.S. Pat. No. 3,996,345, both of which are incorporated herein by reference. Chemiluminescent labels include, for example, those identified in U.S. Pat. No. 4,104,029, also incorporated herein by reference.

Depending on the nature of the label or catalytic signal producing system used, a signal can be detected by means known to those skilled in the art. For example, in the case of a radioactive label, a radiation counter can be used, such as a gamma counter for gamma-emitting markers. For fluorescent labels, a signal can be detected by irradiating with light and observing the level of fluorescence in a fluorometer. For enzyme-catalyzed systems, a color change can be detected visually for a positive reaction when a chromogenic label is used.

The methods of the present invention are also directed to the in vivo detection of cells expressing Queb in a patient. Such methods include the steps of:
(a) administering an antibody having specific reactivity with Queb; and
(b) determining the localization of antibody binding in the patient, wherein the localization of binding indicates the presence of Queb.

As used herein, the terms "patient" and "subject" are used interchangeably to mean any animal, including humans.

The sites of localization can be determined by standard imaging techniques, including, for example, planar imaging, single photon emission computer tomography or by gamma camera whole body imaging. Any suitable imaging agent can be bound to the antibody. Radioisotopes are common imaging agents and include, for example, technetium-99, iodine-123, iodine-125, iodine-131 or a combination of such radioisotopes. The biodistribution of the label is monitored by scintigraphy and accumulations of the label can be related to the presence of the substance to be detected. Whole body imaging techniques are described in U.S. Pat. Nos. 4,036,945 and 4,311,688, which are incorporated herein by reference.

The present invention further provides methods for the diagnosis or a disorder associated with Queuine or a Queuine-containing substance, such as Queuine tRNA deficiency, or the prognosis of a patient having or suspected of having such a disorder. As used herein "disorder" is used interchangeably with the term "disease." As noted previously, decreased levels of Q-tRNA have been observed in malignant cells and in high grade lymphomas compared with Q-tRNA levels in normal cells and low grade lymphomas, respectively, as reported in Randerath et al., *Cancer Res.* 44:1167–1171 (1984); Emmerich et al., Supra; Shindo-Okada et al., *National Products Chemistry* 0:549–558 (1984); Nishimura et al., *Recent Results in Cancer Research* 84:401–412 (1983).

In studies related to the present invention, Q-tRNA levels have been shown to vary among primary human leukemias. However, the level of Q-tRNA deficiency has been correlated with clinical outcome in which highly Q-tRNA deficient patients appeared to have a higher incidence of disease relapse and death.

Figure 2:
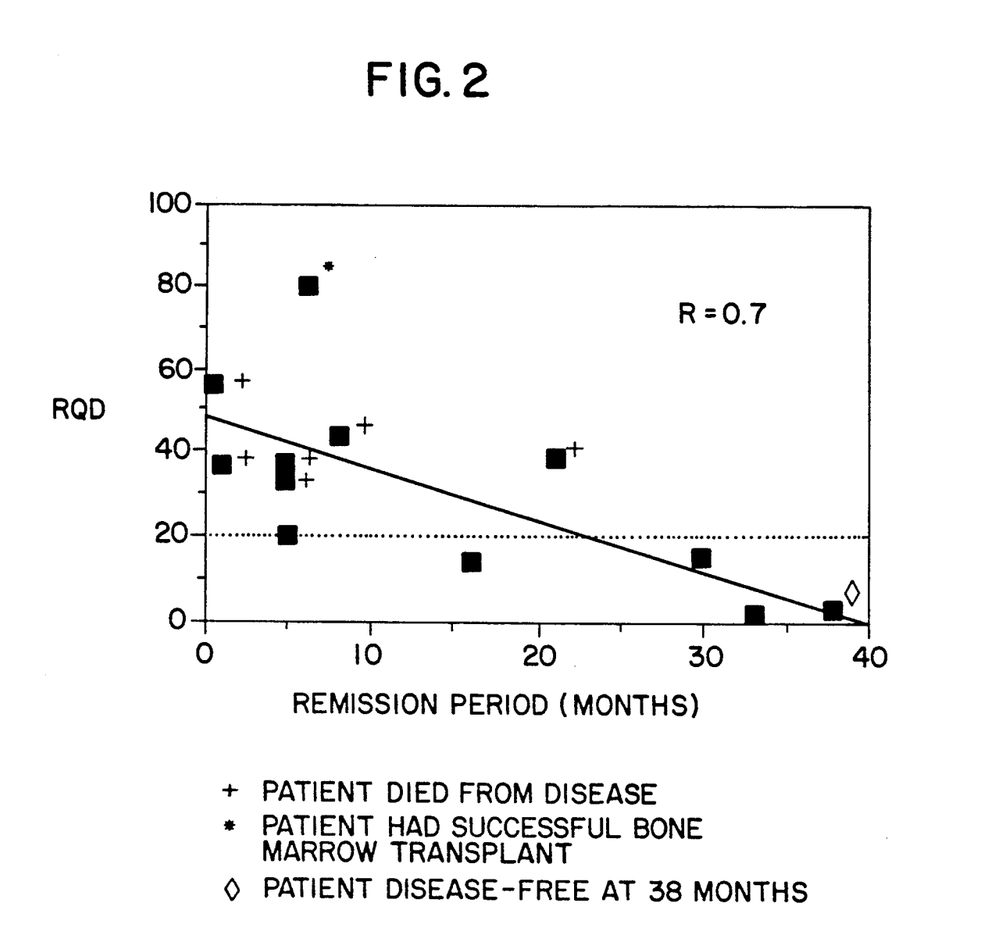
FIG. 2 shows the correlation of RQD with patient remission time.

In these studies, a Relative Queuine Deficiency (RQD) value was given to each of fourteen patients which correlated with the level of Q-tRNA deficiency. RQD indicates the amount of $^3$H-guanine incorporated per $\mu$g of RNA as measured using the tRNA-guanine transglycosylase assay. The RQD in these fourteen patients ranged from 0.7 to 80. In normal donors, the average RQD value for lymphocytes was 3.04±2.73. It was found that the level of Q-tRNA deficiency correlated well with the time of clinical relapse. The data also suggest that patients with RQD values greater than 20 at the time of clinical presentation appeared more likely to die from their disease. The results of these studies are shown in FIG. 2. Other than this measurement, there is no other clinical indication currently known that would allow for this prognosis.

Thus, these studies indicate that the level of Q-tRNA can be used for the diagnosis and prognosis of a patient having a malignant or cell development disorder. The methods of the present invention can accordingly be used for the diagnosis or prognosis of a patient by determining the amount of Queuine incorporated into tRNA and relating the amount to the diagnosis of malignant or cell development disorder or the prognosis of the patient.

The prognostic methods of the present invention can be based on the direct proportional relationship between the amount of polypeptide binding and the amount of Q-tRNA level in a subject. An elevated amount of Q-tRNA, in turn, indicates a favorable prognosis. Thus, the level of Q-tRNA deficiency correlates with the progression or stage of malignancy and with the virulence of malignant cells or tissues. Virulence is a measure of malignancy in which cells having a higher Q-tRNA deficiency are considered malignant and invasive. Thus, the level of Q-tRNA deficiency is used as a risk factor or a prognostic indicator in the methods of the present invention.

The prognostic methods can also be based on the amount of Q-tRNA deficiency as measured by the amount of detectable Queb or Queuine-specific polypeptide that binds to a sample containing tRNA isolated by any method known in the art. In these methods, an amount of binding equivalent to Q-tRNA concentrations in samples having an RQD value of less than about 20, as measured by the guanine transglycosylase assay, indicates a favorable prognosis for an extended remission period and delayed onset of death from disease. By comparison, a reduced amount of binding indicates an unfavorable prognosis. Those skilled in the art can readily determine appropriate methods of converting RQD values into concentrations of Q-tRNA in a sample, which will depend on the detection methodology employed.

Alternatively, the present invention provides more direct methods of determining the prognosis of a patient by relating the amount of Queb in a patient sample with the prognosis of a patient. In these methods, Queb is the direct prognostic indicator such that the Q-tRNA deficiency need not be determined before a prognosis can be made. Those skilled in the art will readily be able to determine the concentration of Queb that corresponds to various disorders.

The discovery of Queb in BAF suggests a mechanism for the high concentration of Queuine in BAF compared with other fluids, including fetal bovine serum. Thus, Queb may serve to retain Queuine in the amniotic fluid by the formation of Queb-Queuine complexes. It appears such complexes and Queb cannot readily pass through the amniotic membrane since Queb is relatively absent in fetal bovine serum.

The presence of Queb and the high concentrations of Queuine in bovine amniotic fluid suggests that Queuine and Queb have a functional role in embryonal development. This suggestion is consistent with a number of recent reports showing that Queuine can influence cell development, Nishimura, *Progress in Nucleic Acid Research and Molecular Biology*, 28:49–73 (1983); French et al., *Proc. Natl. Acad. Sci. USA* 38:370–374 (1991); Langgut and Kersten *FEBS* 265:33–36 (1990). The study by French, et al., supra. has demonstrated that Queuine, through its apparent modification of tRNA, can maintain the pluripotent potential of cells. The studies by Langgut and Kerstein, Supra, also support the suggestion by providing evidence that Queuine may be a substitute for growth factors in a signal transduction pathway.

In studies related to the present invention, Queuine was shown in HL 60 cells (ATCC No. CCL 240) to both stimulate and inhibit (ID$_{50}$ of 7.8 $\mu$M) cell growth and to modulate the ability of cells to respond to differentiation signals at concentrations that do not affect cell growth. These functions are characteristic of agents commonly classed as growth factors.

Due to the binding specificity of Queb, the Queuine-specific polypeptides and antibodies of the present invention for Queuine, such polypeptides are believed to be capable of regulating the biological activity of Queuine. For example, the presence of Queb in cells can act to regulate the insertion of Queuine into tRNA. Given the apparent influence that Queuine insertion into tRNA can have on cell development or function, Queb is accordingly expected to modulate cell behavior. Relatedly, Queb can also regulate the synthesis of proteins encoded by Q-tRNA by regulating the incorporation of Queuine into tRNA.

Although numerous reports suggest that malignant and undifferentiated cells can be Q-tRNA deficient, the mechanism for the deficiency is not yet understood. The deficiency occurs even though the tRNA-guanine transglycosylase is present and free Queuine is available in the circulation. It may be that the Queb gene is activated in malignant cells analogous to other embryonal genes that have been found activated in malignant cells. The activation produces Queb, which results in the complexing of Queuine by the Queb protein thereby reducing Q-tRNA production.

Alternatively, Queb may be more directly involved with malignant expression and embryonal development. In such a case, Queuine, Queuine-containing substances or anti-Queb antibodies can be used to regulate the activity of Queb by forming complexes with Queb. For example, Queb may be analogous to a product that causes malignancy, such as a growth factor encoded by a proto-oncogene. Queuine, Queuine-containing substances or anti-Queb antibodies can serve to inhibit the activity of Queb by reacting with Queb to form inactive complexes.

Thus, the present invention provides methods of using Queuine, Queuine-containing substances, Queuine-specific polypeptides and antibodies to regulate cell development and differentiation. Such methods can be used for preventive or therapeutic purposes by administering an effective amount of Queuine or Queuine-specific polypeptide to a patient sufficient to regulate the activity of Queb or Queuine, respectively. Antibodies specific for Queuine or Queb can also be used. For example, if inhibiting the incorporation of Queuine into tRNA is desired, an effective amount of Queuine-specific polypeptide or antibody sufficient to inhibit such incorporation can be administered. The appropriate dose of Queuine or the polypeptide will depend on the desired level of regulation, which can be readily determined by those skilled in the art.

The reagents in the in vivo methods of the present invention can be administered to a patient by any means known in the art. For example, the reagents can be administered orally, by injection, by infusion or other medically acceptable modes of administration.

Methods of inhibiting or altering the binding affinity of Queuine to Queb are also provided. Such binding can be affected by administering a phorbol ester tumor promoter. Phorbol ester tumor promoters having structural similarity with Queuine are particularly useful in the present invention to alter Queuine's binding affinity with Queb. Such promoters include, for example, teleocidin A, 12-O-tetradecanoyl-phorbol-13-acetate (TPA) and PDD. These phorbol ester tumor promoters can be used, for example, to lower the binding affinity of Queuine and a Queuine-specific polypeptide in the purification methods of the present invention such that a milder eluent can be used.

In studies detailed in Example VII, TPA was shown to reduce the binding affinity of Queuine for Queb. Briefly, TPA at 50% the concentration of Queuine bound to sepharose was evaluated for its ability to antagonize $^{125}$I-Queb binding to Queuine-sepharose. Although TPA did not quantitatively alter the binding of Queb with Queuine at this concentration, Queb was eluted under milder conditions of 20 mM EDTA in the presence of TPA compared with more stringent elution conditions of 8 M urea in the absence of TPA. The results are shown in FIG. 5. Three alternative theories may explain the mechanism by which TPA acts to reduce the binding of Queb to Queuine. First, TPA binds to a part of the Queuine binding site such that Queb can still partially bind Queuine, but the affinity is reduced. Second, TPA binds to and alters the structure of Queb such that the Queuine-binding site is altered. Finally, TPA may cause Queb binding activity to become cation dependent.

The results shown in FIG. 3 also suggest that Queb may be a receptor for phorbol ester tumor promoters, such as TPA. As a receptor for phorbol ester promoters, Queb's ability to bind to such promoters may be reduced if it is complexed to Queuine or a Queuine-containing substance. This suggestion is consistent with studies in which Queuine pretreatment markedly sensitized HL-60 cells to a TPA-induced differentiation response. Although Queuine pretreatment enhances TPA-inducible differentiation, Queuine will also inhibit TPA when used concurrently. These results suggest that Queuine may induce a TPA receptor for which it can also compete.

Another aspect of the present invention is the use of Queb, other Queuine-specific polypeptides or anti-Queuine antibodies as an antidote for toxic Queuine-containing substances. For example, Queuine-containing substances that are potentially toxic may be inserted into tRNA of Queuine-tRNA deficient cells. Thus, by binding such toxic substances with Queb, Queuine-specific proteins or anti-Queuine antibodies to form larger complexes, insertion of such toxic Queuine analogs will be inhibited. Such toxic substances include, for example, Queuine conjugates with toxic molecules such as ricin or radioisotopes as well as other reported analogs as described in U.S. Pat. No. 4,571,423 issued Feb. 18, 1986, to Nomura et al., incorporated herein by reference. Nishimura, *Metabolism* 17:127–136 (1980) and Akimoto et al., *J. Med. Chem.* 29:1749–1753 (1986) also report such analogs and are also incorporated herein by reference. The appropriate dose of a Queuine-specific polypeptide or antibody will depend on the amount of toxic substance to be inhibited and can be readily determined by those skilled in the art.

Finally, the present invention also relates to kits containing Queuine, Queb, other Queuine-specific polypeptides or a combination thereof useful in the methods of the present invention. If required, the kits also contain a signal generating substance to provide or enhance the detection of Queuine, Queb or Queuine-specific polypeptide binding. In addition, other ancillary reagents can be included in such kits, for example, stabilizers, buffers and the like. Such ancillary reagents will depend on the desired assay to be performed or the particular use of the primary reagents. For example, the primary reagents may be mixed with any pharmaceuticallyacceptable carrier known in the art for in vivo uses. Such carriers include, for example, aqueous solutions such as bicarbonate buffers, phosphate buffers, Ringer's solution and physiological saline supplemented with 5% dextrose or human serum albumin.

The following examples are intended to illustrate but not limit the present invention.

EXAMPLE I

Isolation of Queuine

Queuine was isolated from third trimester bovine amniotic fluid (BAF) obtained from Irvine Scientific (Irvine, Calif.) and from Bioproducts for Science, Inc. (Indianapolis, Ind.), using the procedure described in Katze et al., *Science* 216:55–56 (1982). Fetal bovine serum (FBS) was obtained from Tissue Culture Biologicals (Tulare, Calif.). Guanosine, 7-deazaguanine and adenosine were obtained from Sigma Chemical Co. 6-thioguanine was obtained from the National Cancer Institute. TPA, CNBr-activated Sepharose 4B and Sepharose 4B were purchased from Pharmacia (Sweden).

EXAMPLE II

Affinity Separation

The isolation of Queuine binding factors was completed using affinity chromatography. CNBr-activated sepharose 4B (Pharmacia) was coupled with Queuine, guanosine or glycine using the manufacturers described procedure. The coupling ratio of Queuine to the amount of dry sepharose was 2.7 μmole to 0.1 g and the ratio of guanosine to sepharose was 1.3 μmole to 0.1 g. The procedure used targeted coupling of Queuine and guanosine at the 2-amino group of the purine ring.

The affinity-sepharose was equilibrated with phosphate buffered saline (PBS) containing 2 mM $CaCl_2$, and $MgCl_2$ contained in a glass pipette. The sample was allowed to flow through the column containing the affinity-sepharose, and the bound material was eluted with a successive series of PBS buffers (pH 7.5) containing: 20 mM EDTA, 1M NaCl, 1M urea, 8M urea. Once eluted, the protein was precipitated with 95% ethanol containing 0.5M potassium acetate, washed twice in 95% ethanol, and then solubilized in SDS-PAGE sample buffer, 0.25M tris-HCl, pH 6.8; 10% glycerol; 2% SDS; 0.0025% bromophenol blue.

Third trimester BAF (50 ml) was passed over a 0.4 ml Queuine-sepharose column. The column was then washed with PBS containing 2mM of $CaCl_2$ and $MgCl_2$ until the eluent contained <0.01 OD (280 nm). Protein bound to the column was successively eluted with PBS containing: 20 mM EDTA, 1M NaCl, 1M urea and 8M urea. Eluent fractions (200 μl) were collected and spectrophotometrically monitored (280 nm). The majority of the bound material was observed to elute with 8M urea, with much lesser amounts of material observed with the other washes.

The peak areas of each eluent were collected, the protein was precipitated by 95% ETOH/0.1M potassium acetate, washed in 95% ethanol, lyophilized, and solubilized in PAGE buffer. The material was then loaded on 15% SDS-PAGE gels, electrophoresed and stained with Coomassie blue R-250. FIG. 1 illustrates these results. Large molecular weight material (>90 kD) was found in the 1M NaCl, 1M urea and 8M urea eluents. Small bands were irregularly noted at approximately 50 kD and 70 kD in the 8M urea eluent, and to a lessor extent 1M urea and 1M NaCl eluents. The 8M urea eluent contained a predominant band that migrated at approximately the 23 kD size which has been designated hereon as "Queb." The Queb band was consistently observed in all isolations (n>20) Further, Queb was primarily only eluted with 8M urea.

To determine if Queb was present in serum, the experiments as described above were completed with fetal bovine serum (FBS). There was significant binding of FBS material to the Queuine-sepharose column, which eluted with each of the washes applied. The electrophoretic profile illustrated that the material eluted with each wash, was identical, suggesting nonspecific binding. Further, there was a distinct absence in any of the elutions of Queb. These results indicate that Queb found in BAF was not significantly measurable in FBS using this procedure.

EXAMPLE III

Isolation of Guanosine-binding Proteins by Affinity Chromatography

Queuine is a 7-deazaguanine class of purine. The interrelationship of Queuine and guanine has been demonstrated by their shared substrate affinities for the tRNA-guanine transglycosylase as reported in Okada & Nishimura, *J. Biol. Chem.* 254:3061–3066 (1978). To determine if Queb isolated with the Queuine-sepharose column was specific to Queuine, a guanosine-sepharose column was prepared and analogous experiments as those presented with Queuine-sepharose in Example II were completed with both BAF and FBS. Material was observed to bind to the guanosine-sepharose column from both BAF and FBS. As was observed with the Queuine-sepharose column, large molecular material (>90 kD) from BAF was eluted by 1M NaCl and 8M urea. Also, similar to that observed with Queuine-sepharose column in FIG. 1, the 50 kD and 70 kD range proteins were observed to be eluted with the different wash buffers. However, there was no presence of Queb that bound with high affinity to the guanosine column, suggesting that Queb binds Queuine, but not guanosine.

The analysis of FBS with guanosine-sepharose affinity chromatography resulted in a binding profile identical to that observed for the Queuine-sepharose. This result indicates that the binding proteins that exist in FBS cannot discriminate between Queuine and guanosine. Also, based on their elution with all of the elution washes, the binding of the FBS proteins to guanosine is nonspecific.

EXAMPLE IV

Iodination of Queb

IODO-GEN was purchased from Pierce, (Rockford, Ill.) $Na^{125}I$ (2.57 Ci/M mole) was obtained from New England Nuclear, Wilmington, Del. The $^{125}I$-labelling of isolated Queb was completed by a standard procedure using IODO-GEN at room temperature according to the manufacturer's directions.

EXAMPLE V

Binding Specificity of the Queb

Queb was isolated from the 15% SDS-PA gels by electroelution, and labelled with $^{125}I$ according to Example IV. The pure $^{125}I$-Queb (53 Ci/m mole) was then examined for its ability to bind to Queuine-sepharose relative to glycine-sepharose or guanosine-sepharose. Equal quantities ($1 \times 10^6$ cpm, 50 μl) of $^{125}I$-Queb were incubated for 2 hours with equal aliquots (50 μl) of ligand-sepharose. The buffer was then isolated and the sepharose was washed with PBS until less than 1×10⁴ cpm were measured in the eluent. The amount of unbound $^{125}$I-Queb collected in these buffers, and the amount of sepharose-bound $^{125}$I-Queb was quantitated. $^{125}$I-Queb bound to the Queuine-sepharose with high efficiency, as approximately 67% of the available $^{125}$I-Queb appeared to bind with the Queuine-sepharose. This was in sharp contrast to the minimal amount of $^{125}$I-Queb binding to glycine-sepharose and guanine-sepharose.

Table 1 summarizes the results of these studies. These results demonstrate that the 23K protein has high affinity for Queuine, and based on its inability to bind to guanosine-sepharose, good selectivity as well.

TABLE 1

Binding Specificity of $^{125}$I-23K to Queuine-sepharose Compared with Glycine-sepharose and Guanosine-sepharose

| Ligand | Unbound[a] CPM | Bound[b] CPM | Total CPM | % Bound |
|---|---|---|---|---|
| Glycine | 802,682 ± 92,380 | 70,500 ± 8,800 | 872,880 | 8.08 |
| Guanosine | 843,385 ± 128,280 | 104,740 ± 12,885 | 948,125 | 11.05 |
| Queuine | 404,060 ± 77,970 | 851,350 ± 91,830 | 1,255,410 | 67.8 |

[a]CPM measured in the supernatant and three pBS/Ca$^{++}$, Mg$^{++}$ washes. n = 3; ± S.D.
[b]CPM measured associated with sepharose following removal of supernatant and three PBS/Ca$^{++}$, Mg$^{++}$ washes. n = 3; ± S.D.

The bound $^{125}$I material was successively eluted with PBS containing 20mM EDTA, 1M NaCl, 1M urea and 8M urea, and analyzed by gel electrophoresis. The $^{125}$I-Queb that bound to the Queuine-sepharose was only eluted by 8M urea. No $^{125}$I-Queb was found eluted from the guanosine-sepharose.

Another observation was the apparent formation of dimer and trimers of the $^{125}$I-Queb. This appears to occur with time following the purification of the Queb. The electrophoretic analysis shows that although the dimer and trimers are both present in the starting material, only the dimer and native Queb are shown eluted by the 8M urea.

EXAMPLE VI

Sequence Analysis of Queb

Queb was isolated by electroelution from 10% polyacrylamide gels. Attempts were then made to obtain the N-terminal sequence of Queb. This proved unsuccessful as the amino-terminus appear to be "blocked".

Attempts were then made to obtain an internal sequence of Queb. Pure Queb (8 μg) was digested (22 hours) using endoproteinase Lys-C (5 μg) to cleave internally at the C-terminus of lysine residues. The Lys-C digest was then electrophoresed (16% PAGE, Tris-tricine) which resulted in the identification of approximately 10 bands. The gel was electroblotted to ProBlott paper and the transferred peptide bands visualized by staining with 0.1% Coomassie blue in 40% MeOH/0.1% acetic acid. Bands selected were cut out and the peptide fragment analyzed using a Protein Sequences Model 475A (Applied Biosystems, Foster City, Calif.).

The band that migrated at an approximate molecular weight of 16.5 kD produced quantifiable results with an internal peptide sequence of: EGSDNQPNGXTNPN. Searches were completed for analogous references in the Proteins Information Source and in Swiss-Protein Data Bank. No match was found with any existing known sequence.

EXAMPLE VII

Effect of TPA on $^{125}$I-Queb Binding

Figure 3A:
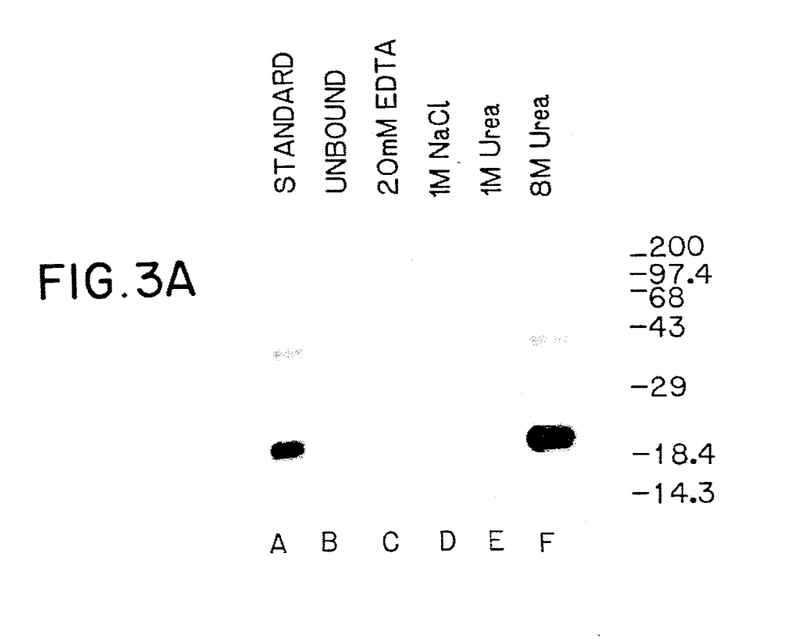
FIGS. 3A and 3B show the binding affinity of Queb for Queuine-sepharose in the absence of TPA (A) and in the presence of TPA (B).
Figure 3B:
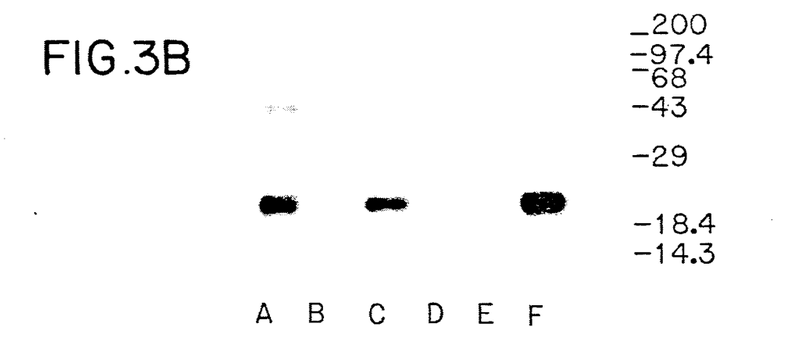

TPA, at 50% of the concentration of the Queuine bound to sepharose, was evaluated for its ability to antagonize $^{125}$I-Queb binding to Queuine-sepharose. FIG. 3A illustrates the $^{125}$I-Queb binding without TPA and FIG. 3B illustrates the results with TPA. As observed in lane B, very little of the $^{125}$I-Queb was found to be "unbound" either with or without TPA. This correlates with previous results which demonstrated that TPA did not quantitatively alter $^{125}$I-Queb binding. However, the elution patterns of $^{125}$I-Queb from the Queuine-sepharose was altered in the TPA samples. As observed in lane C, 20 mM EDTA was able to elute $^{125}$I-Queb from Queuine-sepharose when TPA was present in the binding assay. This result suggests that the Queb binding affinity had been altered by TPA, although not necessarily antagonized.

The foregoing description of the invention is exemplary for purposes of illustration and explanation. It will be apparent to those skilled in the art that changes and modifications will be possible without departing from the spirit or scope of the invention. It is intended that the following claims be interpreted to embrace all such changes and modifications.

---

SEQUENCE LISTING ( 1 ) GENERAL INFORMATION:

( i i i ) NUMBER OF SEQUENCES: 1

( 2 ) INFORMATION FOR SEQID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO (v) FRAGMENT TYPE: N-terminal (xi) SEQUENCE DESCRIPTION: SEQ ID NO:1:

Glu Gly Ser Asp Asn Gln Pro Asn Gly Xaa Thr Asn Pro Asn
1               5                   10

I claim:

1. A substantially pure non-antibody polypeptide having specific binding reactivity with Queuine said polypeptide having a molecular weight of about 23 kD.

2. A substantially pure non-antibody peptide having specific binding reactivity with Queuine, said peptide containing an amino acid sequence of substantially the sequence EGSDNQPNGXTNPN.

3. A method for purifying a non-antibody polypeptide having specific binding reactivity with Queuine, comprising:

(a) contacting a sample containing said polypeptide with insolubilized Queuine or antibody having specific reactivity with said polypeptide;
(b) separating bound polypeptide from unbound components of the sample;
(c) detaching bound polypeptide from the insolubilized Queuine or antibody; and
(d) collecting purified polypeptide.

4. The method of claim 3, wherein said polypeptide is a Queuine-specific protein having a molecular weight of about 23 kD or a fragment thereof.

5. The method of claim 3, further comprising the step of adding an effective amount of a phorbol ester tumor promoter after step (b) to reduce the binding affinity of said polypeptide for the insolubilized Queuine.

* * * * *

UNITED STATES PATENT AND TRADEMARK OFFICE
CERTIFICATE OF CORRECTION

PATENT NO. : 5,312,900

DATED : May 17, 1994

INVENTOR(S) : R. Douglas Armstrong

It is certified that error appears in the above-identified patent and that said Letters Patent is hereby corrected as shown below:

Column 1, line 12, please insert after "7-deaza" and before "mammalian cells" --guanine analog. Although it is found in all normal--.

Column 9, line 37, please delete "National Products Chemistry" and replace therefore with --Natural Products Chemistry--.

Column 15, line 26, please delete "three pBS/CA++" and replace therefore with --three PBS/CA++--.

Signed and Sealed this

Eighth Day of November, 1994

Attest:

*Attesting Officer*

BRUCE LEHMAN

*Commissioner of Patents and Trademarks*